United States Patent [19]

Nicholson

[11] Patent Number: 5,256,065
[45] Date of Patent: * Oct. 26, 1993

[54] ACID ETCH FOR DENTAL TREATMENTS

[76] Inventor: James A. Nicholson, 120 S. 28th Ave., Hattiesburg, Miss. 39401

[*] Notice: The portion of the term of this patent subsequent to Oct. 29, 2008 has been disclaimed.

[21] Appl. No.: 784,314

[22] Filed: Oct. 29, 1991

Related U.S. Application Data

[63] Continuation-in-part of Ser. No. 434,291, Nov. 13, 1989, Pat. No. 5,061,183.

[51] Int. Cl.$^5$ ................................................ A61C 5/00
[52] U.S. Cl. ...................................... 433/228.1; 433/9
[58] Field of Search ................................. 433/228.1, 9

[56] References Cited

U.S. PATENT DOCUMENTS 4,010,545  3/1977  Kilian et al. ........................... 433/9

OTHER PUBLICATIONS

*Carrier Res.*: 2-26 (1974), Journal of the European Organization for Carries Research, vol. 8, No. 1, 1974, "Fissure Sealants, Laboratory Studies" by Silverstone, note pp. 6-9.

Primary Examiner—Vincent Millin
Assistant Examiner—J. Doyle
Attorney, Agent, or Firm—Dowell & Dowell

[57] ABSTRACT

A solution or gel for use in etching the surfaces of teeth in preparation for the application of dental restoratives. This etchant contains phosphoric acid in an amount not to exceed approximately 5% by weight.

6 Claims, No Drawings

ACID ETCH FOR DENTAL TREATMENTS

CROSS REFERENCE TO RELATED APPLICATIONS

This application is a continuation-in-part application of Ser. No. 07/434,291, filed Nov. 13, 1989, and entitled Acid Etch for Bonding Ceramic Orthodontic Brackets, and is to be issued Oct. 29, 1991 as United States Patent 5,061,183.

FIELD OF THE INVENTION

This invention is generally directed to acid etch solutions which are used in preparing the surfaces of teeth prior to their repair or filing using conventional dental restoratives and more specifically to either a solution or gel etch which contains minor amounts of phosphoric acid. The amount of phosphoric acid in the etchant should not exceed approximately 5% by weight of the solution or gel compound and preferably should be within a range of approximately 2.0% to 5.0%. The acid etchant of the present invention is specifically designed to prepare enamel, dentin or cementum tooth surfaces for the application of dental fillings and restorative materials. The solution is specifically formulated to permit sufficient etching of internal and external tooth surfaces so as to insure a strong and secure bond of the dental restoratives to the tooth surfaces without causing harm to adjacent exterior enamel of the tooth or dentin along the gum line of a patient.

The exact percent of phosphoric acid in solution or in the gel compound may vary depending upon the particular restorative or application.

HISTORY OF THE RELATED ART

In preparing teeth for dental restorations including repair of chipped or broken teeth, cracked enamel and the like, it is first necessary that the affected area be prepared. This may be done by either an invasive or non-invasive manner. The invasive manner is normal cavity preparation with a high or low speed drill, or laser, whereas, the non-invasive method is by etching the desired area directly. If cleaning of the area is necessary, this may be accomplished by using a prophy brush with a flour-of-pumis and water solution after which the surface of the tooth is thoroughly rinsed and dried utilizing compressed air. Thereafter, the surface to which the dental restorative is to be applied is etched with an acidic etching solution with the application of the etching solution being made utilizing small cotton processor pellets. The etching solution is applied for approximately 60 seconds, after which the etching solution is rinsed thoroughly with water and the surface of the tooth again dried. The acid etch is applied to the tooth in order to slightly roughen the tooth surface so as to promote an effective bonding of an applied restorative bonding agent or agents.

In conventional acid etch solutions which incorporate phosphoric acid, the amount of phosphoric acid is normally present in a range between approximately 37% to 50% by weight in solution or in a gel compound. Although the use of such conventional phosphoric acid etchants has been generally acceptable in practice, there are potential problems which may result from such treatment. In some instances, the application of conventional acid etchants may result in the removal of enamel adjacent the area being treated, thus creating a potential for future tooth decay or enamel failure such as cracks or pitting of the enamel. In other instances, such as when a surface restoration is being performed to exposed dentin along a patient's gum line, the use of strong acid etchants may be detrimental to the dentin or living tissue in the pulp chamber of the tooth.

SUMMARY OF THE INVENTION

This invention is directed to an acid etchant which may be either in liquid or gel form and which includes a phosphoric acid which is present in solution in an amount not to exceed 5% by weight. More preferably, the phosphoric acid should be present by weight in the amount between 0.51% and 5.00%, with approximately 3.00% being preferred for consistent bond strength. The acid etchant of the present invention is applied for approximately one minute on permanent teeth utilizing a gentle wiping action with the liquid being applied by a cotton pad or pellet. When in gel form, the gel may be applied to the surface of the tooth for a selected time, such as approximately one minute, after which the gel is removed from the surface of the tooth by rinsing with water while the area is aspirated and thereafter the surface dried thoroughly with warm air.

It is a primary object of the present invention to provide a phosphoric or buffered phosphoric acid solution or gel which may be used as an acid etch for preparing the surface of teeth for repair or restoration utilizing conventional dental restoratives and which allows the restorative to be securely bonded to the teeth during treatment without destruction to adjacent tooth surface enamel and without enamel fracture or pitting.

It is another object of the present invention to provide a phosphoric or buffered phosphoric acid etch solution which may be utilized in treating exposed dentin area of teeth without significant disturbance of the dentin.

It is also an object of the present invention to provide an acid etchant which utilizes only a minor amount of phosphoric acid in the etching solution or gel compound and which thereby maintains the surface enamel of a tooth in a healthier state by reducing the amount of disruption to the tooth enamel while still allowing optimum bond strength to be achieved between the dental restorative and the tooth surfaces.

DESCRIPTION OF THE PREFERRED EMBODIMENT

In applicant's copending United States patent application Ser. No. 07/434,291, filed Nov. 13, 1989, now U.S. Pat. No. 5,061,183 and entitled Acrd Etch for Bonding Ceramic Orthodontic Brackets, an acid etchant is disclosed which was specifically formulated in order to avoid the problems which are inherent in bonding orthodontic brackets to the surface of teeth and in particularly, to problems associated with removing orthodontic brackets after patient treatment. Before the advent of the acid etch solution of the referenced copending application there were frequent occurrences of damage to tooth enamel or even fracturing of teeth during the process of removing the bonded brackets. In an attempt to overcome the problem associated with orthodontic bracket removal, tests were made in order to determine whether or not there was a direct correlation between the surface treatment or preparation and the resulting bond strength obtained utilizing conventional orthodontic bonding adhesives and bonding systems. Tests were conducted in which the concentration of phosphoric acid in an acid etch solution was varied prior to applying the acid etch solutions to the surface of teeth in preparation for orthodontic bracket bonding. As a result of those tests it was learned that the amount of phosphoric acid in solution could be significantly reduced while maintaining sufficient bond strengths to allow the orthodontic brackets to be positively retained during the course of patient treatment.

As previously discussed, conventional acid etch solutions of the phosphoric acid type normally include the phosphoric acid in ranges between 37% to 50% by weight. However, from the test made with regard to altering the acid etch solutions for use in preparing the surface of teeth for orthodontic bracket bonding, it was learned that the amount of acid could be reduced to as little as 0.51% and still obtain consistent bond strength. The overall findings from the test indicated that acid etch solutions in the range from approximately 0.51% to approximately 5.40% resulted in acid etch solutions which could be used to effectively prepare the surface of teeth and yet resulted in solutions in which the orthodontic brackets could be removed following patient treatment without damage to surface tooth enamel.

During the tests the bonding agents being utilized included photo-polymerizable restorative materials conventionally used in dental practice. Therefore, the results obtained in adjusting the acidity of the acid etch solutions were determined to have a direct correlation between the bond strength of the dental restoratives as they would be utilized in conventional dental practice to repair or fill cracked, chipped, or other damaged teeth.

The results of the acid etch dilution tests which were performed for orthodontics are set forth in the following table:

TABLE "A"

| DILUTIONS $H_3PO_4$ TO $H_2O$ | ACID ETCH DILUTION TESTS RESULTING PERCENT OF $H_3PO_4$ | RESULT |
|---|---|---|
| 1-0 | 43.00% | A |
| 1-1 | 21.50% | A |
| 1-2 | 10.80% | A |
| 1-4 | 5.40% | B |
| 1-8 | 2.70% | B |
| 1-16 | 1.35% | B |
| 1-24 | 1.02% | C |
| 1-28 | 0.85% | C |
| 1-30 | 0.76% | C |
| 1-32 | 0.68% | C |
| 1-48 | 0.51% | D |
| 1-64 | 0.34% | E |

A = bond strength too great, possible result of damage to surface enamel or tooth structure.
B = some brackets removable, others only removable with excessive force or requiring filing.
C = brackets easily removed utilizing conventional orthodontic tools.
D = some brackets not sufficiently retained to surface of teeth causing premature displacement of brackets.
E = numerous brackets not sufficiently retained to surface of teeth.

The phosphoric acid solutions utilized in performing the tests disclosed in Table "A" utilized a buffered phosphoric acid in water. It is envisioned that the etching solutions may include other non-active etching ingredients other than phosphoric acid and yet still fall within the teachings of the present invention which indicate an optimum range for the amount of phosphoric acid by weight which can be in solution to perform surface etching of teeth in preparation for dental repairs and restorations. Additives such as fluoride may be added to the etchant solution to improve its acceptability to practitioners.

In addition to the foregoing, the tests were conducted in such a manner that the acid etch solutions were applied to the surface of teeth by utilizing cotton pads or pellets which are gently wiped across the surface of the tooth in the area to be treated or restored for a period of approximately 30 to 120 seconds for permanent and deciduous teeth and preferably between approximately 30 to 60 seconds. At all times during the application of the etching solution a visible layer of the solution should be present and the solution should not be allowed to dry on the surface of a tooth.

Once the surface of the tooth has been treated with the acid etch solution or gel, the tooth is rinsed with water while the area is aspirated and thereafter the area is thoroughly dried with warm air.

As with conventional phosphoric acid etches, care should be taken to avoid skin contact or contact with oral mucosa and eyes to prevent possible injury to the patient.

Although the phosphoric acid may be utilized in aqueous solutions which may include other agents which are not active in the etching of the surface of tooth, the solutions may be created in gel form by adding thickeners t the phosphoric acid solution to increase the viscosity of the solutions. In this manner, gel-like products may be obtained which may be applied to the surface of teeth. By way of example, the phosphoric acid solutions may be blended with hydrophilic silicates, fumed silicates or gelatin which may be present in solution in an amount of approximately 5% or more by weight.

From the results, it should be noted that, for use as dental restoratives, the lower concentrated acid etch solutions would not be effective as the tests indicated that the dental restoratives were too easily removed when utilized as a bonding agent to adhere bonding brackets to teeth. The conventional solutions, as mentioned above, would range from 43% and upward. However, as previously discussed, the use of conventional strength acid etch solutions often results in excess removal of surface enamel in the area of the tooth being treated and may result in pitting or damage to dentin or pulp tissue which would otherwise be in a healthy condition. Therefore, from the tests made with respect to orthodontic brackets it can be determined that sufficient bond strengths are possible utilizing acid etch solutions having a very low percentage of phosphoric acid in solution.

In this regard, it is necessary to determine an optimum range to satisfy both the necessity for the restorative material to bond to the existing tooth surface and to obtain an acid etch solution that would have minimal adverse effect on tooth enamel. From the tests, the effective acid etch solution should contain phosphoric acid in the range of approximately 1.35% to 5.4%, with an optimum being in the range of 2% to 5%.

In order to verify that the dental restoratives could be utilized with the weaker phosphoric acid solutions, various acid etchants were prepared containing from 2.0% to 5.0% phosphoric acid in solution or in appropriate gel. The tests were made utilizing bovine teeth in which an area to be restored, utilizing self cure and photo-polymerizable materials, was first prepared and subsequently treated with the weaker phosphoric acid etch solutions. In making the tests, the tooth site was first prepared and if necessary cleaned utilizing a flourof-pumis and water solution after which the site was air dried. Thereafter the weak acid etchant was applied for approximately one minute and thereafter the composition is washed away, and then air dried. A base material such as calcium hydroxide may, in some cases, be placed on the portion of the tooth to be restored. A thin layer of unfilled resin was then placed on the site of the restoration and air dried. The restorative material, which in the test made was a photo-polymerizable material, was then applied to the site and initially shaped. As a photo-polymerizable material was used, a curing light was thereafter applied to achieve the desired cure. The restored area was further contoured into a final shape and the site air dried. A final layer of unfilled resin may, in some cases, be placed over the restored area, and, if the unfilled resin is photo-polymerizable, the light is applied to accomplish final curing.

The etchant solutions and gels of the present invention may be utilized to prepare teeth for restorations including. Such restorative materials include Bis-GMA composition including "CONCISE", "ADAPTIVE", "SILUX", "HERCULITE" and "PRISMA"; dentin bonding compositions including "SCOTCHBOND" and "PRISMA"; dentin bonding compositions including "SCOTCHBOND" and "PRISMA UNIVERSAL BOND"; and glass ionomers including "KETAC" and "VITREBOND". conventional restorative materials may be used as well.

As previously discussed, in order to assure both an optimum bonding strength of the dental restorative and to cause minimal disruption to the tooth enamel, it is believed that the phosphoric acid in solution or in the gel compound should be present in at least 2% to approximately 5% by weight.

It is further believed that utilizing the teachings of the present invention that if it is possible to use the more dilute phosphoric acid solutions in the dental repair of the surface of teeth adjacent a patient's gum line including areas where there may be exposed dentin. Conventional phosphoric acid solutions are detrimental to the living tissue in the pulp which is accessed through the dentin. However, the weak phosphoric acid solutions of the present invention including those in the range of 0.51% to approximately 2% do not have the same damaging effect and therefor may be useful in preparing areas for periodontic treatment of the dentin surface of teeth without adversely effecting the living tissue of the pulp.

I claim:

1. A method of etching the surface of a tooth in preparation for repair using dental restoratives comprising the steps of; applying to the surface of the tooth an acid etch solution having phosphoric acid present in solution in an amount between 0.51% to 5.40% by weight, thereafter rinsing the surface of the tooth and drying the surface of the tooth.

2. The method of claim 1 in which the acid etch is applied to the surface of the tooth for periods between approximately 30 to 60 seconds.

3. The method of claim 1 in which the acid etch solution contains sufficient fillers to form a gel.

4. An acid etchant for treating the surfaces of teeth prior to the application of dental restoratives comprising a solution containing phosphoric acid as the active etching ingredients wherein the phosphoric acid is present in solution in an amount not to exceed approximately 5.4% by weight and wherein the solution contains sufficient fillers to form a gel.

5. The etchant composition of claim 4, wherein the phosphoric acid is present in solution in an amount of at least approximately 0.51%.

6. The etchant composition of claim 4, wherein the phosphoric acid is present in an amount of at least approximately 1.35%.

* * * * *